US008948861B2

(12) United States Patent
Rai et al.

(10) Patent No.: US 8,948,861 B2
(45) Date of Patent: Feb. 3, 2015

(54) METHODS AND SYSTEMS FOR DETERMINING OPTIMUM WAKE TIME

(75) Inventors: Deepti Dunichand Rai, Mumbal (IN); Steven F. Kalik, Arlington, MA (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 397 days.

(21) Appl. No.: 13/077,557

(22) Filed: Mar. 31, 2011

(65) Prior Publication Data
US 2012/0253220 A1   Oct. 4, 2012

(51) Int. Cl.
*A61B 5/0476* (2006.01)
*A61B 5/00* (2006.01)

(52) U.S. Cl.
CPC .............. *A61B 5/0476* (2013.01); *A61B 5/4806* (2013.01)
USPC ........... 600/545; 600/301; 600/544; 340/540; 340/575

(58) Field of Classification Search
CPC .. A61B 5/0476; A61B 5/4806; A61B 5/4809; A61B 5/4812; A61M 2021/0083; A61M 2230/10
USPC ................... 600/544, 545; 340/575
See application file for complete search history.

(56) References Cited

U.S. PATENT DOCUMENTS

| | | | |
|---|---|---|---|
| 4,228,806 A | 10/1980 | Lidow | |
| 5,928,133 A | 7/1999 | Halyak | |
| 6,928,031 B1 * | 8/2005 | Kanevsky et al. | 368/12 |
| 7,248,915 B2 * | 7/2007 | Ronnholm | 600/544 |
| 8,179,270 B2 * | 5/2012 | Rai et al. | 340/575 |
| 2002/0080035 A1 * | 6/2002 | Youdenko | 340/573.1 |
| 2005/0177031 A1 * | 8/2005 | Hursh | 600/300 |
| 2006/0235315 A1 * | 10/2006 | Akselrod et al. | 600/509 |
| 2006/0293602 A1 * | 12/2006 | Clark | 600/500 |
| 2006/0293608 A1 * | 12/2006 | Rothman et al. | 600/545 |
| 2007/0249952 A1 * | 10/2007 | Rubin et al. | 600/544 |
| 2009/0207028 A1 * | 8/2009 | Kubey et al. | 340/575 |
| 2010/0152546 A1 * | 6/2010 | Behan et al. | 600/301 |
| 2011/0018720 A1 * | 1/2011 | Rai et al. | 340/575 |

OTHER PUBLICATIONS

Merica et al. "State transitions between wake and sleep, and within the ultradian cycle, with focus on the link to neuronal activity." Sleep Medicine Reviews (2004) 8, 473-485.*
Gath et al. "Classical Sleep Stages and the Spectral Content of the EEG Signal." Intern. J. Neuroscience. 1983. vol. 22. pp. 147-156.*
(Continued)

*Primary Examiner* — Navin Natnithithadha
*Assistant Examiner* — Meredith Weare
(74) *Attorney, Agent, or Firm* — Christopher G. Darrow; Young Basile Hanlon & MacFarlane, P.C.

(57) ABSTRACT

A system for determining optimum wake time is disclosed whereby the system comprising includes a receiver for receiving electroencephalogram (EEG) data. The system further includes a processor configured to generate at least one frequency band based on the EEG data received, wherein the processor is further configured to determine an optimum wake time based on a relative low point on the at least one frequency band. The system also includes an indicator configured to provide notification of the optimum wake time.

17 Claims, 7 Drawing Sheets

(56) References Cited

OTHER PUBLICATIONS

"An Alarm Clock Designed to Wake the Sleeper at a Point in His/Her Sleep Cycle When He/She Will Feel the Most Refreshed and Alert." Nov. 21, 2005. 6 pages.*

Merica, Helli et al., State transitions between wake and sleep, and within ultradian cycle, with focus on the link to neuronal activity, Physiological Review, 2004, pp. 473-485.

* cited by examiner

METHODS AND SYSTEMS FOR DETERMINING OPTIMUM WAKE TIME

TECHNICAL FIELD

The present disclosure relates generally to the field of monitoring sleep and wake conditions, and more specifically, to methods and systems for providing optimum wake time(s).

BACKGROUND

For any task or occupation, sleep deprivation can result in the decline of alertness levels, thereby resulting in the degradation of work performance. To this end, sleeping may be considered an effective countermeasure to prevent decline in alertness levels. A possible drawback of a sleep period may be sleep inertia, which is the feeling of grogginess or post awakening performance degradation. The recovery effect of sleep may depend on various factors related to sleep including sleep duration and wake time, which may determine sleep inertia. Furthermore, the positive effects of sleeping can depend on, various factors such as the duration of sleep, the sleep-wake history, and the stage of sleep from which a person awakens. Depending upon the user allotted time for sleep, including sleep start time and sleep duration, an estimation of the optimum wake time may allow a user to resume his/her work at an optimal performance level with minimal post awakening performance degradation.

Though sleep patterns may vary, it is generally accepted that individuals pass through various stages during sleep, called sleep stages. Typically, sleep may be categorized into either Rapid Eye Movement (REM) sleep or non-REM (NREM) sleep. NREM sleep may be associated with four sleep stages, with sleep stages 1 and 2 corresponding to lighter sleep and sleep stages 3 and 4 corresponding to deeper sleep. Generally, sleep inertia is a function of increasing sleep stage. Thus, waking a person from a lighter stage of sleep, such as stage 1, may result in less sleep inertia than waking a person from a deeper stage of sleep.

Literature has suggested that the power of the delta wave ("delta power"), as measured by an electroencephalogram (EEG), may correspond to sleep depth as indicated by one of the various sleep stages. A delta wave is a type of brain wave with a specific frequency range. Delta power decreases in REM sleep and increases through NREM sleep stages 1, with the highest delta power typically being associated with NREM stage 4. However, even within a sleep stage, delta power will vary. Delta power also varies based on the duration of sleep and sleep-wake history. For example, an estimated optimum wake time may differ for a sleep duration of forty minutes as compared to a sleep duration of eight hours.

In some instances, only a short period of time is allocated for a sleep period. Therefore, as sleeping may provide significant improvements in alertness levels, measuring delta power to determine the ideal wake time to afford minimum sleep inertia may be important to maximizing the recovery effects of sleeping. While a number of biological alarms that monitor sleep patterns of a user are available on the market, these alarms are primarily concerned with reducing the effects of sleep inertia associated with waking up from night time sleep period. Some products, for example, focus on scanning for a user's light stages of sleep (Stages 1 and 2) in the sleep cycle and waking up the user during or near these moments or near the user's scheduled wake time. In effect, these products use bodily activity patterns to attempt to estimate the sleep stage in order to wake a person during the lightest sleep stage. Since there is very little bodily activity in deeper stages of sleep, current products fail to recommend wake times in those stages. Further, current products do not take into consideration variability of distinct frequency bands, such as ones indicating delta power within each sleep stage and assume that as a user transitions from light sleep to deep sleep, there is a steady rise in delta power. Thus, current products do not recommend wake times in deep stages of sleep as they presume this may result in higher sleep inertia. Additionally, few current designs offer the ability to collect brain activity patterns, such as delta waves, from a user. Without the ability to collect brain activity data, current designs do not offer the ability to adapt the optimal wake time selection to match a user's brain activity, and fail to recommend optimal wake times within a sleep cycle. Products that incorporate the collection of brain activity patterns may use the data to determine a transition into or out of REM sleep, and wake the user at the transition point. These products assume that sleep inertia is at a maximum during deep stages of sleep, and again fail to consider the variability of delta power within a sleep stage.

Thus, a need exists for systems and methods for providing optimum wake time(s) based on fluctuations in brain activity frequencies to minimize sleep inertia. Such systems and methods monitor and/or determine sleep conditions which may improve alertness such as by maximizing sleep duration, minimizing sleep inertia after awakening, and/or minimizing wake inertia as users prepare to fall asleep. In addition, such systems and methods may determine optimum wake time(s) within a single sleep stage as well as between successive sleep stages. Further, by offering the ability to directly collect brain activity patterns from a user, systems and methods disclosed herein may determine optimum wake time(s) based on a user's ongoing brain activity.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

One aspect of the disclosure provides a system for determining optimum wake time. The system includes a receiver for receiving electroencephalogram (EEG) data, and a processor configured to generate at least one frequency band based on the EEG data received, wherein the processor is configured to determine the optimum wake time based on a relative low point on the at least one frequency band. The system also includes an indicator configured to provide notification of the optimum wake time.

Another aspect of the disclosure provides a system for determining optimum wake time. The system includes a receiver for receiving electroencephalogram (EEG) data and a processor configured to generate a delta power rhythm associated with sleep depth based on the EEG data received, wherein the processor determines an optimum wake time based on a relative low point on the delta power rhythm, the relative low point corresponding to a wake time resulting in minimal sleep inertia. The system further includes an indicator configured to provide the optimum wake time.

Yet another aspect of the present disclosure provides a method for determining optimum wake time. The method includes receiving electroencephalogram (EEG) data via a receiver and generating at least one frequency band based on the EEG data received. The method also includes determining an optimum wake time based on a relative low point on the at least one frequency band, the relative low point corresponding to a wake time resulting in minimal sleep inertia. The method further includes providing an indication of optimum wake time.

BRIEF DESCRIPTION OF THE DRAWINGS

For detailed understanding of the present disclosure, references should be made to the following detailed description of the several aspects, taken in conjunction with the accompanying drawings, in which like elements have been given like numerals and wherein.

DETAILED DESCRIPTION

Before the present systems, methods, and computer-readable media are described, it is to be understood that this disclosure is not limited to the particular systems, methods and media described, as such may vary. Also, the present disclosure is not limited in its application to the details of construction, arrangement or order of components and/or steps set forth in the following description or illustrated in the figures. Thus, the disclosure is capable of other aspects, embodiments or implementations or being carried out/practiced in various other ways.

One of ordinary skill in the art should understand that the terminology used herein is for the purpose of describing possible aspects, embodiments and/or implementations only, and is not intended to limit the scope of the present disclosure which will be limited only by the appended claims. Further, use of terms such as "including", "comprising", "having", "containing", "involving", "consisting", and variations thereof are meant to encompass the listed thereafter and equivalents thereof as well as additional items.

It must also be noted that as used herein and in the appended claims, the singular forms "a," "and," and "the" may include plural referents unless the context clearly dictates otherwise. Thus, for example, reference to "a device" refers to one or several devices and reference to "a method of monitoring" includes reference to equivalent steps and methods known to those skilled in the art, and so forth.

Figure 1:
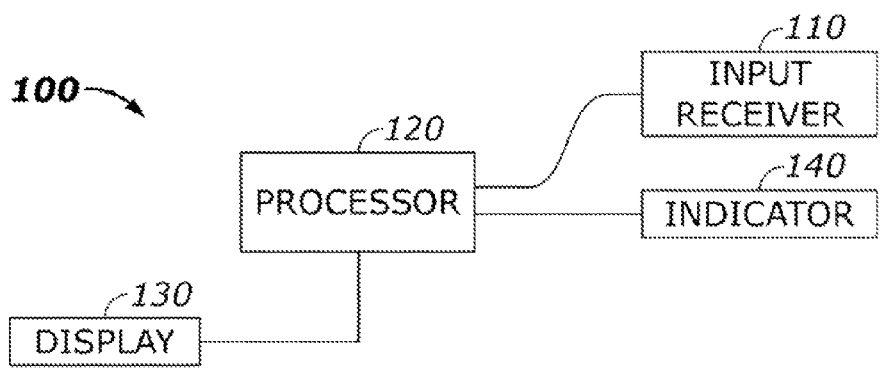
FIG. 1 provides a schematic illustrating a system for providing wake time(s) in accordance with one aspect of the present disclosure.

Moving now to FIG. 1, a general schematic is provided depicting a system, indicated generally at 100, for monitoring sleep conditions and/or providing wake time(s). Throughout the present disclosure, the system 100 may be referred to as a sleep scheduler, delta alarm or sleep monitoring device. The system 100 may include any instrumentality or aggregate of instrumentalities operable to compute, classify, process, transmit, receive, retrieve, originate, store, display, detect, record, reproduce, handle, or utilize any form of information related to sleep and/or wake conditions of a user. Information in the form of data, signals, or the like, may be received by a receiver or input receiver 110 (to be described below) communicatively coupled to a processor 120. The processor 120 may comprise a microprocessor, minicomputer, or any other suitable device, including combinations and/or a plurality thereof, for executing instructions related to the handling of the data from the receiver 110. Based on parameters, instructions, algorithms, programs, or the like, the processor 120 may output information via a display 130 or an indicator 140 to notify a user, for example, of a particular sleep or wake condition (e.g., optimum wake time).

Figure 2:
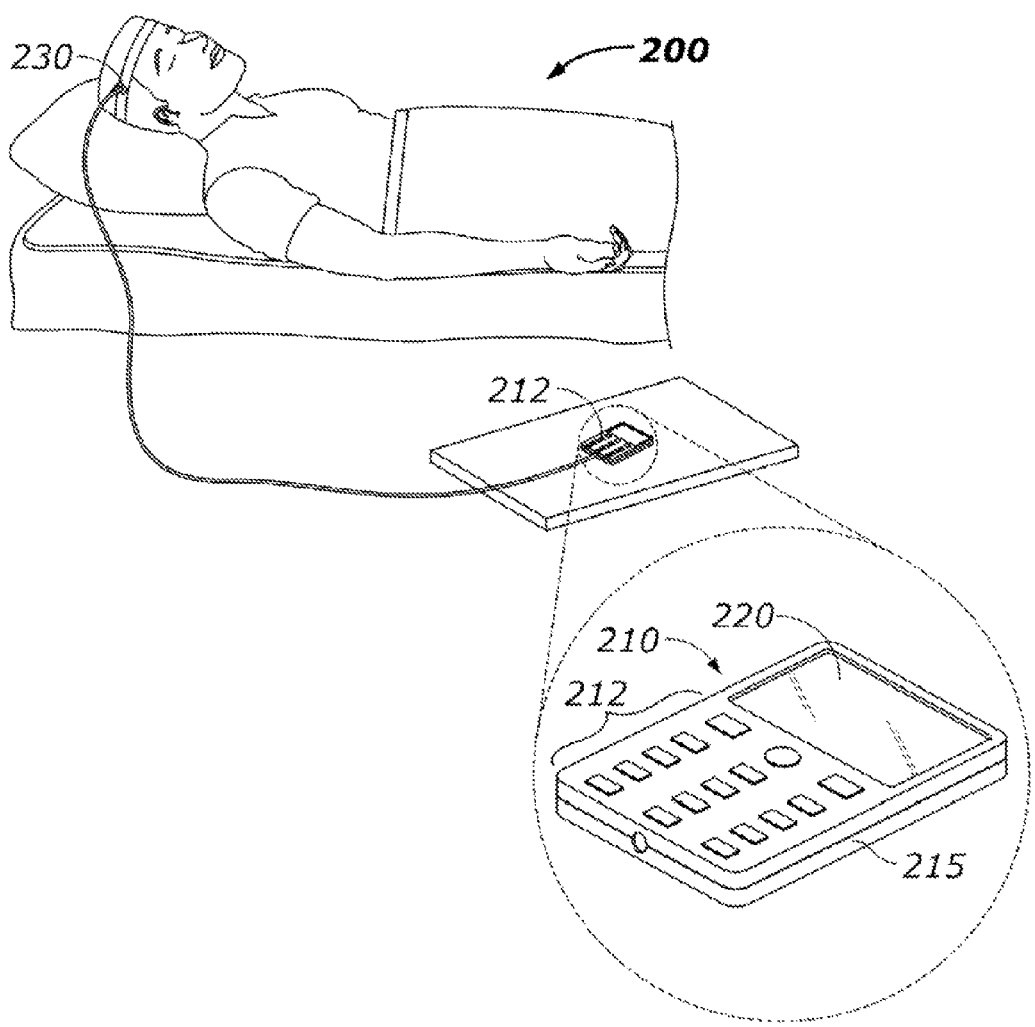
FIG. 2 provides a schematic illustrating one implementation of the system in FIG. 1.

Turning now to FIG. 2, one possible implementation of a system for providing sleep or wake conditions is shown. The system for monitoring and/or providing sleep conditions is shown as a delta alarm 210, as one example. In the implementation shown, the delta alarm 210 may be any electronic device disposed within a housing 215 or may be included on any electronic device. For example, the delta alarm 210 may be included as part of a personal digital assistant (PDA) or wristwatch.

The delta alarm 210 may include a receiver 110 in the form of a keypad 212, for example, for receiving an input from a user 200 in some implementations. Although the input receiver 110 is shown in FIG. 2 as a keypad 212, various forms of the input receiver 110 may include a keyboard, a button, a trackwheel, or other suitable means for a user to input or select information to be received by the delta alarm 210. According to another implementation, a receiver 110 may comprise a sensor 230, such as an electrode, for example, operable to receive an input in the form of a signal. Various types of input or information to be received by the delta alarm 210 may further include data associated with the user's brain activity, sleep and wake states or sleep parameters such as sleep start time, wake time, sleep duration, estimated alertness level, type of task, projected alertness requirement associated with a task or the like.

An example of data received by the sensor 230 is an electroencephalogram (EEG) signal, recorded with standard wet or dry EEG electrode methods. An EEG may be a device that measures and records electrical activity in the brain. To this end, an input receiver 110 or sensor 230, such as an electrode, for example, may be attached to a user and also coupled to a computer via an amplification system to monitor brain activity. Data from the EEG can be collected and filtered by the processor 120 into particular frequency bands as well known to those skilled in the art of recording and analyzing EEG activity. Frequency bands may include, for example, the delta band, sigma band, and beta band, among others. For example, sigma bands and/or closely associated brain signals known as spindle oscillations, may peak in power during a light sleep stage approximately 10-20 minutes after sleep onset. In regards to sleep stages, sleep may be categorized into either Rapid Eye Movement (REM) sleep or non-REM (NREM) sleep. NREM sleep may be associated with four sleep stages, with sleep stages 1 and 2 indicating a lighter sleep and sleep stages 3 and 4 indicating a deeper sleep.

Another example is a beta band which decreases as sleep enters a deeper stage. The typical frequency range for signals in the delta band is 0.5-4 Hz, which may typically be the dominant EEG activity during deep sleep stages (e.g., Stage 3, Stage 4). Once the signals have been filtered into particular frequency bands, calculations may be performed on a data group from a frequency band or the data may be plotted graphically to observe patterns. For example, frequency band data may be plotted against sleep cycles, duration of sleep, time of day, etc.

Input(s) received by the delta alarm 210 may be converted to signals to be handled by a processor 120 of the delta alarm 210. Conventional analog or digital circuits may utilize such signals to estimate when a nap will be required for a user and/or when to awaken a user from the nap.

The delta alarm 210 may also include a display 220 such as a liquid crystal display (LCD) or the like. The display 220 may show information including a user's sleep and wake conditions, optimum wake time, or any of the aforementioned data, either inputted by a user, sensed by a sensor 230, determined by the delta alarm 210, provided by another source (e.g., computer) or store of such data, or produced by other means.

Figure 3:
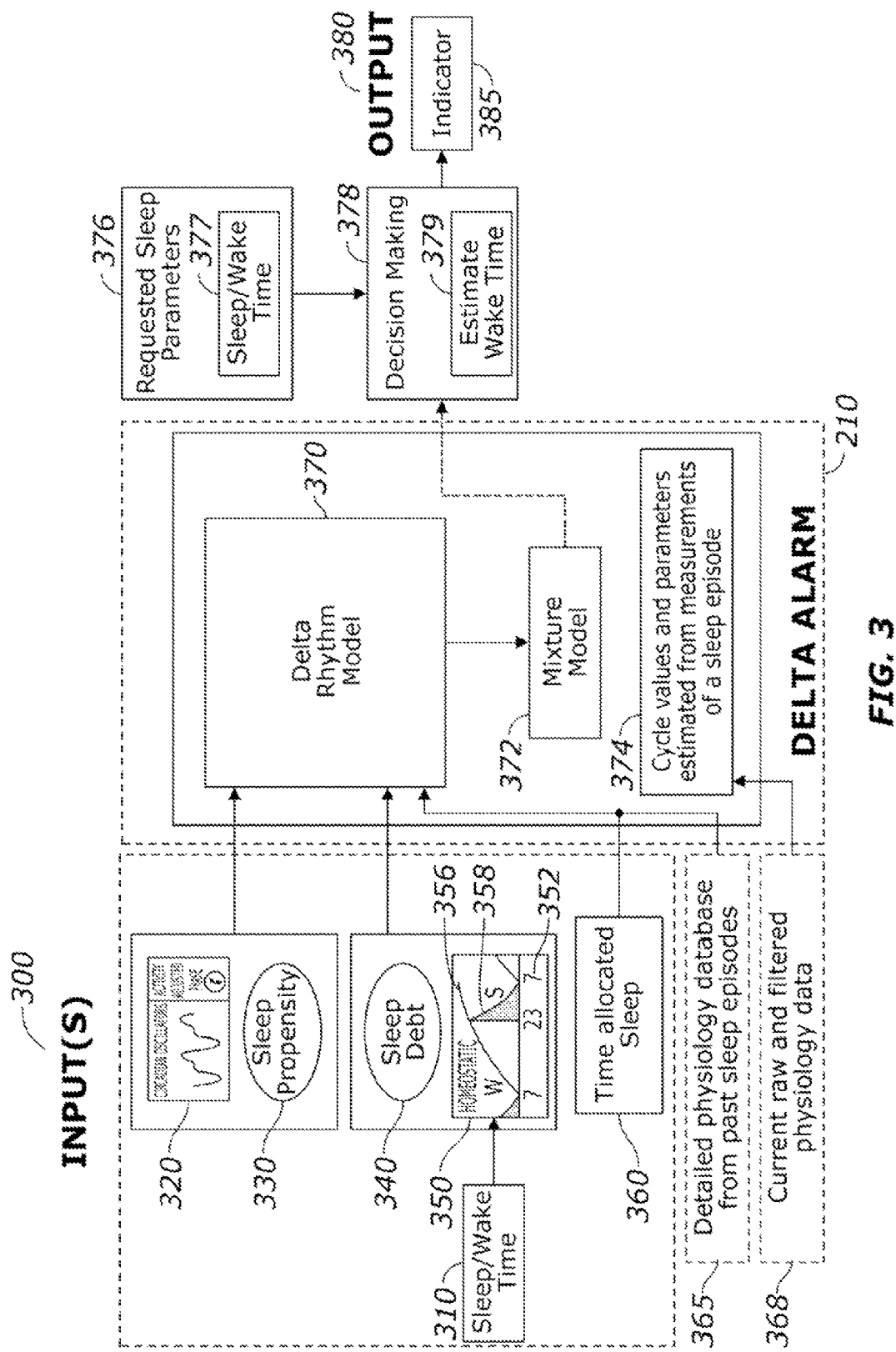
FIG. 3 provides illustrative inputs and outputs for the system of FIG. 1.

Referring now to FIG. 3, an illustration is provided depicting inputs 300 and outputs 380 for the delta alarm 210 of FIG. 2. Inputs 300 in the form of sleep/wake time(s) 310 may be received or sensed by the delta alarm 210 such as by the receiver 110 and/or sensor(s) 230 as previously described. Sleep/wake time(s) 310 may include a sleep start time corresponding to the time a user falls asleep and wake time corresponding to the time the user wakes up from a sleep period or a series of such events. It should also be noted that as used herein, a sleep period can occur for any length of time including, but not limited to, typical sleep during the night (i.e., duration of continuous sleep exceeding 6 hrs) and/or taking a nap (i.e., shorter duration(s) of continuous sleep in increments ranging from minutes to 1 or more hours). Additionally, inputs 300 may include, and are not limited to, information such as requested sleep parameters 376 such as desired sleep duration, experimental data from other users, and past sleep data 365. Past sleep data 365 may include data indicating when a user last slept and woke, and the duration of that sleep period, along with more detailed data such as EEG data, detailed physiology data, or any other data the delta alarm may have received from past sleep periods. This past sleep data 365 may be stored in the form of a database in the delta alarm or in other generic forms of storage media. Inputs 300 may also be in the form of real-time data 368 collected by various input means such as sensors 230 or the like. Real-time data 368 and past sleep data 365 may be combined. Real-time data 368 collected may later become past sleep data 365 as new real-time data 368 becomes available.

Depending on the sleep/wake time(s) 310 sensed, the delta alarm 210 may determine a user's homeostasis in order to determine an optimum wake time for the user. In one implementation, a homeostatic model 350 may be used to simulate a user's sleep pressure according to the amount of wake time 356 and sleep time 358 resulting from recent sleep/wake time(s) 310 received by the delta alarm 210. According to the homeostatic model 350, sleep pressure may be expressed with respect to the time of day 352. Under this framework, a sleep pressure of zero, for example, may indicate a level of homeostasis within the user. In addition, as illustrated by the homeostatic model 350, sleep pressure may be a logarithmic function of wake time 356. Thus, the longer a person is awake, the further the person's body departs homeostasis. On the other hand, the sleep time may be an exponential decay of sleep pressure with respect to time of day 352 back to homeostasis. Further, the rate at which sleep pressure returns back to homeostasis during the sleep time 358 may be significantly quicker than increasing sleep pressure during the wake time 350.

Sleep debt 340 may be affected by sleep/wake time(s) 310 received by the delta alarm 210. Sleep debt 340 generally refers to the probability of falling asleep based on past sleep-wake history (i.e., time since recent sleep and duration of recent sleep), and independent other factors, such as overall time of day, which can have effects separate from the effect of time since the last sleep period. Sleep debt 340 may also correspond to any sleep deficit a user possesses, or in other words, how much sleep a user's body is owed. Thus, sleep debt 340 may be based on a user's sleep/wake parameters, history, and/or conditions, such as sleep/wake time(s) 310. In one implementation, a user's sleep debt 340 may be modeled on an eight-hour sleep cycle whereby a user may sleep eight hours a day to maintain homeostasis within the body. In another implementation, an EEG may be used to estimate sleep debt 340.

As shown in FIG. 3, inputs 300 such as past sleep data 365 and a user's homeostatic model 350 will determine a delta rhythm model 370. For a particular user under a certain set of conditions, a delta rhythm model 370 comprises information from sleep-wake history used to simulate curves representing sleep debt 340 and sleep propensity 330 (to be discussed below). In cases of greater sleep debt 340, delta rhythm model 370 will be observed with a user quickly sinking into deeper stages of sleep and spending less time in a light sleep stage.

Other inputs 300 such as sleep propensity 330 and circadian oscillators 320, for example, may influence the delta rhythm model 370. Sleep propensity 330 may correspond to the likelihood of a user falling asleep at a particular time of day, or as a function of the light/dark cycle to which the user is exposed. This sleep propensity 330 is distinguished from the sleep debt 340 in that the sleep debt 340 is the probability of falling asleep based on past sleep-wake history (i.e., time since recent sleep and duration of that sleep), independent of the effects of light/dark cycle or overall time of day expressed by sleep propensity 330. Sleeping at a time when the sleep propensity 330 is high (i.e., drive for sleep is high), can result in greater delta power as opposed to sleeping at a time where the sleep propensity is low.

Generally, during each NREM episode, a sleeper may transition towards and away from deep sleep. Therefore, rather than experiencing a steady rise in delta power through the sleep episode, a delta power rhythm may exhibit high points (e.g., peaks) and low points (e.g., troughs) in delta power. Specifically, within a given model or power rhythm and within a given time frame, a relative low point or relative high point may be found. A relative low point may be the lowest point within a particular time range but not be the lowest point in an entire power rhythm, for example. Therefore, multiple relative low points may exists within a given power rhythm. Thus, it may be possible to wake up a sleeper during deeper stages of sleep when the delta power is near a relative low point or lowest point and still afford minimal sleep inertia for the sleeper.

Additionally, sleep propensity 330 may be measured by a circadian oscillator 320, which may simulate the circadian rhythm of an average user in a particular light/dark cycle, or of a specific user existing within or transitioning between the light/dark cycles of particular time zones. The circadian rhythm refers generally to the fluctuations of physical and mental characteristics associated with a 24-hour day-night cycle. A person's sleep-wake cycle history may be an example of a circadian rhythm and may, in some instances, be referred to as a person's "internal clock." To this end, the circadian oscillator 320 may use the time of day, the amount of sunlight exposure, temperature and other factors to simulate a user's circadian rhythm and thereby determine the sleep propensity 330 of the user.

In one implementation, a circadian oscillator 320 may be a device separate from the delta alarm 210 including a processor that simulates the circadian rhythm of a user. In another implementation, the circadian oscillator 320 may be a standalone program/simulation within the processor of the system 100. In any physical implementation, a circadian oscillator 320 may receive input(s) from at least one sensor. Typical information received, sensed, and/or recorded by the sensor(s) may include, but are not limited to, time of day, length of sunlight exposure or temperature, or the like. Information received by the sensor(s) may be utilized by the circadian oscillator 320 to output the circadian rhythm which can be used to compute the sleep propensity 330. The circadian oscillator 320 of a user should be taken into account when estimating optimal sleep/wake conditions. An example of a situation where this would be important is after travel to a different time zone. A user may find that at a usual sleep time in the new local time zone, his or her sleep propensity 330 is higher or lower than typical due to the time zone change. If the user's sleep propensity 330 is lower, then more time in lighter stages of sleep, more time spent transitioning into deeper stages of sleep, and a reduction in delta power may all be observed. Hence a user's circadian oscillator 320 should be taken into consideration when estimating optimal sleep/wake conditions.

Further as shown, time allocated for a sleep period 360 as provided by a user may be another input 300 received by the delta alarm 210. In certain implementations, a user may input a sleep start time, sleep wake time, sleep duration as examples of time allocated for a sleep period 360.

Other possible inputs 300 may include current real-time data 368 in the form of raw and filtered physiology data, such as tables and or data from real-time measurements of actual physical/brain activity from a user. Such inputs 300 may affect how fast oscillations occur within the delta rhythm model 370 depending on a given sleep propensity 330 and/or sleep debt 340. The aforementioned current real-time data 368 may be received via a sensor 230 (e.g., electrode) in contact with a user to measure actual physical/brain activity. A real-time measurement element of the delta alarm 210 may be enabled whereby EEG data (e.g., signals) are collected by the real-time measurement element of the sensor 230 and filtered into power bands such as delta power (1-4 Hz), sigma power (12-17 Hz), beta power (12-24 Hz), and other bands familiar to those skilled in the art of EEG recording and sleep research. The power bands are further analyzed to identify variations in the power found in such frequency bands and to detect peaks and troughs in the power bands to support the prediction and estimation of waking times providing optimal recovery and refreshment.

Continuing with FIG. 3, the delta alarm 210 may generate a delta rhythm model, shown generally at 370, comprising information on sleep-wake history utilizing inputs 300. Over the course of a sleep period or sleep cycle, the pattern in delta power changes as influenced by sleep-wake history. As previously mentioned, sleep-wake history relates to previous times when the user was last asleep and last awake.

The delta rhythm model 370 is shown as a generally increasing curve with generally increasing normalized delta power values (to be described in detail below) corresponding to a person progressing into deeper stages of sleep. Conversely, as the person enters lighter stages of sleep or REM sleep, the curve approaches generally decreasing normalized delta power values. In other words, delta power generally increases as one progresses through successive NREM sleep, i.e., Stage 1 to Stage 2 to Stage 3 to Stage 4, and generally decreases as one enters REM sleep. These cycles may repeat over the course of a sleep period, with the delta power values increasing in cycles associated with deeper stages of sleep. At the height of increasing normalized delta power values may be a peak in the delta rhythm model 370, whereas a trough may lie at a low point of the delta rhythm model 370 curve. Further, within a given sleep stage for an individual user, delta power displays peaks and troughs in a rhythmic pattern as opposed to increasing or decreasing steadily throughout the sleep stage. Peaks within a sleep stage indicate times at which it might be optimal to wake a user. By way of example, a user may have a peak in delta power in a light phase of sleep, and this light phase of sleep might be viewed as an optimal time to wake a user. However, less sleep inertia may result if the wake time were delayed until the delta power troughs, even if the delta power troughs in a deeper stage of sleep. A person who has not slept for long enough duration or has not slept in a long period of time, and thus has a larger sleep debt or long wake history, may spend more time in deep sleep. Hence, the delta rhythm model 370 may display higher amplitude and shallower troughs than for someone who has just awoken from a satisfying sleep.

Requested sleep parameters 376, such as a user's sleep/wake time 377 or sleep/wake history, may also be manually inputted into the delta alarm 210. The delta alarm 210, specifically the delta rhythm model 370 generated by the delta alarm 210, may undergo a decision making 378 process to provide an estimate wake time 379. To this end, during the decision making 378 process, EEG data from the user is filtered into different frequency bands, such as delta bands. Thus, delta band data collected using an EEG for a user may show the fluctuations in delta power within one or successive sleep cycles. The delta power data (e.g., bands) received by the delta alarm 210 may be utilized to generate an estimate wake time 379 correlating to an optimum wake time. Generally, optimum wake time correlates to a wake time which provides a user or subject the quickest recovery, greatest refreshment, or some other preferred combination of local and global recovery of performance following a sleep period. For example, an optimum wake time during a sleep period may be the wake up time which results in minimal sleep inertia for the user. A power profile generated may be used to estimate the optimum wake time such as waking up a user near the trough of the EEG power profile, resulting in lesser sleep inertia and thereby increasing the amount of recovery obtained from the nap or sleep period. The power profile generated from these frequency bands is compared to dominant frequency data available from the sleep history data of the user. Depending on the sleep time entered by the user, the optimum wake time will be calculated. As mentioned, an optimum wake time may correspond to a wake up time whereby a user experiences the lowest possible sleep inertia (e.g., grogginess) once awakened from the sleep period. The effects of sleep inertia may vary between sleep stages as well as within each particular sleep stage.

Systems and methods disclosed herein utilize the frequency of dominant oscillation of power in the band of interest, such as the delta band, for example. Generally, the frequency of dominant oscillation may refer to the oscillation of the change in amplitude of the signal power for signals filtered by the processor. A dominant oscillation of power, which determines a relative low point in a particular model (e.g., power rhythm), is typically very slow (i.e., seconds to minutes in period). Such dominant oscillation of power may be used to predict when the relative low point in closest proximity to the optimum wake time will occur. In the case of more than one relative low point, relative low point A may be selected since the low point A may correspond to a wake time that is closer to the user's desired sleep duration than relative low point B, despite low point B being an absolute minimum. Further, systems and methods herein may possess some predictive capability for locating and utilizing a frequency of dominant oscillation of power in at least one frequency band. The processor may predict when a relative low point will occur, before or near the desired sleep duration or wake time.

By way of example only, a user may desire a nap time of 20 minutes and thus will enter 20 minutes into the delta alarm 210. A decision making 378 algorithm executed by the delta alarm 210 will check for parameters including the dominant frequency from the sleep history data and the real time power profile of the EEG. The user then falls asleep and as the nap time approaches 20 minutes, the decision making 378 algorithm will check if the real time EEG power profile is close to a lowest point (i.e., minima, trough). If so, an alarm or some other indicator 385 will be initiated. Alternatively, if the user had selected a desired nap time of 35 minutes, then the delta alarm 210 utilizing the decision making 378 algorithm would not initiate an alarm at 20 minutes but rather the algorithm would wait until the EEG power profile is at its next lowest point (e.g., 40 minutes). Thus, it is ensured that the user will awaken at a lowest point thereby ensuring minimal sleep inertia and maximum recovery from a nap.

The delta alarm 210 may utilize a user's delta rhythm model 370 in order to determine an optimum wake time for the user. A delta power model 370 is a mathematical model used to predict the peaks and the troughs of the delta power rhythm for a particular user. In one implementation, a delta rhythm model 370 may be simulated using a user's sleep data received by the delta alarm 210 from at least one previous sleep. For example, the delta rhythm model 370 may be based on EEG data collected from when the user slept for 6 hours at a particular time the previous night. The resulting delta rhythm model 370 may then predict peaks and troughs in delta power at certain specific times. In another implementation, the delta rhythm model 370 may exhibit traits of a mixture model 372 based on real-time data 368 collected and modeled as it is received. The resulting mixture model 372 may predict peaks and troughs in delta power at certain other specific times that may or may not be the same as those predicted by the delta rhythm model 370 based on past history data. In one implementation, the delta rhythm model 370 is based on past history data, but adapts as real-time data 368 is received and included in a mixture model 372. For example, a delta rhythm model 370 based on past history may predict that a first trough in delta power will occur at 7 minutes into a sleep period, and a second trough will appear at 23 minutes. However, the delta alarm receives real-time data 368 through the EEG input that indicates that the first trough was reached at 6.5 minutes into the sleep period. Subsequently, the mixture model 372 may predict that the second delta power trough will occur at 22 minutes rather than at 23 minutes.

As such, a delta rhythm model 370 that combines past sleep data 365 with real-time data 368 may be referred to as a mixture model 372. In a mixture model 372, past sleep data 365 and real-time data 368 may be given particular weight in the mathematical model. The weight specified for past sleep data 365 and real-time data 368, respectively, may change over the course of time. In one implementation, more weight may be assigned to real-time data 368 as the delta rhythm model 370 gains more real-time data 368 over time. In another implementation, sleep cycle values (e.g., sleep duration, etc.) and parameters 374 may be estimated from measurements (e.g., EEG data) of a sleep period, incorporating real-time data 368 to derive the mixture model 372.

As previously mentioned, literature has suggested that delta power is proportional to sleep depth. Delta power generally increases as a person progresses through the stages of NREM sleep toward deeper stages of sleep and decreases when a person is in REM sleep. Typically, a delta rhythm model 370 for a single user does not appear as continuously increasing or decreasing curve, but rather a curve with peaks (P) and troughs (T). These peaks and troughs represent the variations of delta power within one sleep cycle. Waking a person at or near the trough of the delta power rhythm as opposed to at or near the peak of the delta power rhythm is likely to result in quicker recovery and greater refreshment from the sleep period. Refreshment may be measured as a score of feeling good after a sleep period or period. Peaks in a delta rhythm model 370 represent times whereby waking a user will result in high sleep inertia effects. Thus, the delta alarm 210 will avoid waking a user during those times which correlate to the peaks in a delta rhythm model 370 whereby sleep inertia (i.e., grogginess) is relatively high.

The estimate wake time 379, such as an optimum wake time, may be one form of output 380 provided by the delta alarm 210. Given a subject's sleep-wake history, along with time allocated for a sleep period 360, the delta alarm 210 may estimate the optimum wake time by approximating the intensity of sleep inertia if the subject is awakened at that time and the time it will take for the performance degradation effect (i.e., sleep inertia) to fade away.

The delta alarm 210 may provide any suitable indicator 385 to provide notification of the optimum wake time. Further, the indicator 385 may provide information to a user as to an ideal time to wait for sleep inertia dissipation prior to resuming work following a sleep period. For example, the delta alarm 210 may calculate an estimated sleep inertia in addition to indicating an optimum wake time, therefore alerting a user as to when to resume work. In the event that an optimum wake time is determined, an indicator 385, such as digital data shown on the display of the delta alarm 210, may suffice to alert a user when to awaken from a sleep period. In other implementations, indicators of an optimum wake time may be in the form a light, sound (e.g., buzzer, alarm), vibration, or any other suitable indicator to wake a user from a period of sleep.

Figure 4:
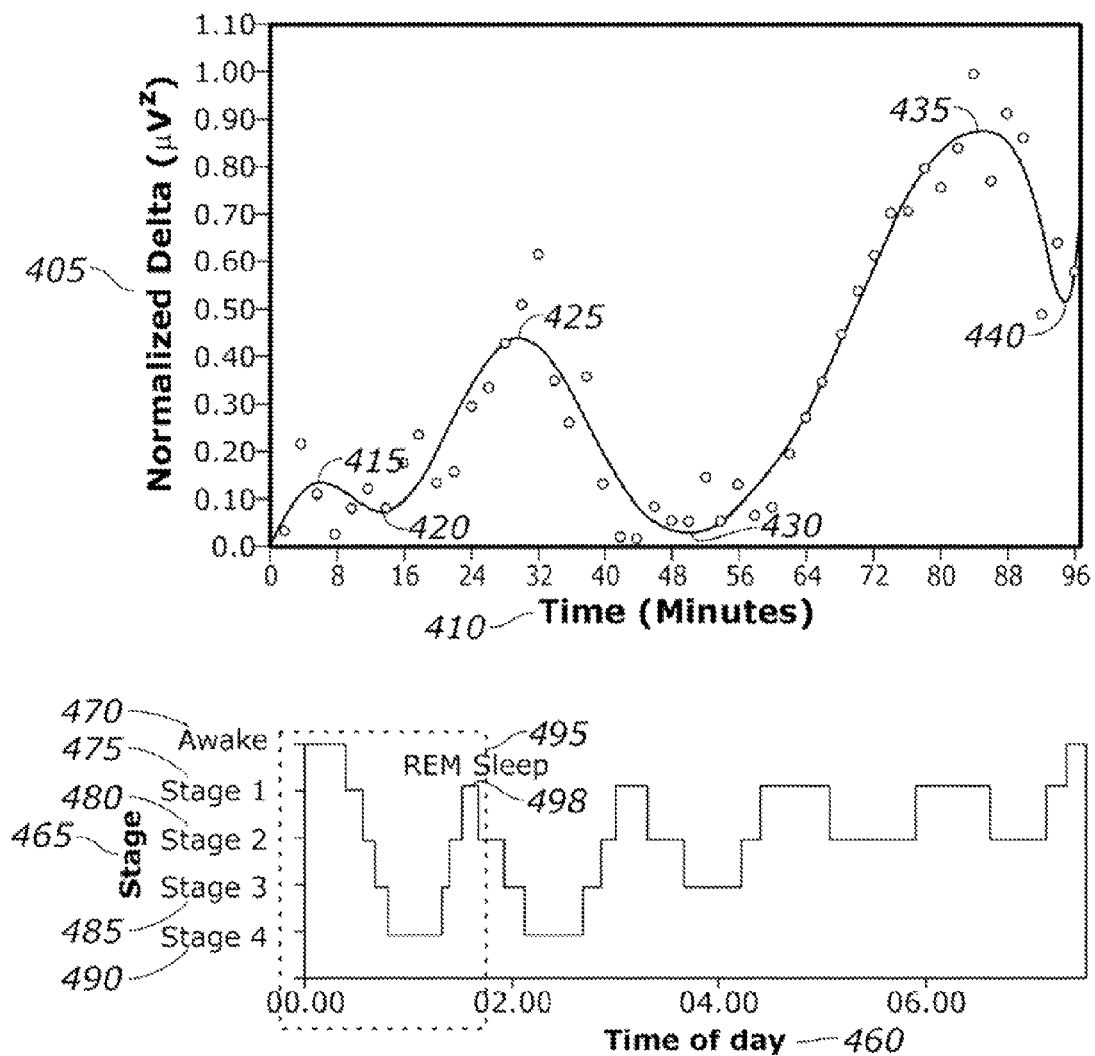
FIG. 4 provides data representing a delta power rhythm during a sleep period corresponding to sleep stages and the time of day.

Turning now to FIG. 4, schematic is provided illustrating a delta power rhythm 370 exhibited by a single subject or user during a sleep period corresponding to sleep stages and the time of day. As used herein, the delta rhythm model 370 of FIG. 3 may also be referred to as a delta power rhythm. Specifically, FIG. 4 depicts the time course of delta power within a first NREM sleep cycle for a single user. The delta power, as indicated by normalized delta 405 in units of $\mu V^2$ and plotted against time 410 in minutes is generally proportional to sleep debt 340. The normalized delta 405 is normalized to the largest amount of delta power found in a NREM cycle. The delta rhythm model 370 is depicted as a curve with various troughs 420, 430, 440 and peaks 415, 425, 435 progressing along stages of a NREM sleep cycle, from 0% to 100% of the sleep cycle. As depicted by FIG. 4 only, a trough 420 at approximately 10% of the NREM sleep cycle would correspond to an optimum wake time of 15 minutes into a sleep period allotted to last approximately 100 minutes. The troughs 420, 430, and 440 correlate to optimum wake times within the single NREM sleep cycle at which times a user may experience great recovery and refreshment if awakened from a sleep period.

Further in FIG. 4, sleep stages are shown plotted against time of day 460 in increments of 2 hours. Therefore, within a sleep cycle lasting approximately 6 hours, a user may progress through various sleep NREM sleep stages 465 including Stage 1 (S1) 475, Stage 2 (S2) 480, Stage 3 (S3) 485, Stage 4 (S4) 490, REM sleep stage 498, as well as an awake stage 470. Box 495 depicts the aforementioned sleep stages within the first NREM to REM cycle of a night time sleep period. A REM sleep stage 498, corresponding to a high brain activity relative to NREM sleep stages 475, 480, 485, 490, may be found as one approaches 100% of the NREM cycle over which delta rhythm model 370 is shown in FIG. 4. Generally, the delta power should gradually increase along S1-S4, reaching its high point at S4, then decrease as transitions are made from S4-S2-REM.

As shown in the top figure of FIG. 4, the troughs 420, 430, 440, respectively, within the delta rhythm model 370, therefore each indicate chances to awaken the user with reduced sleep inertia or grogginess. The top figure in FIG. 4 depicts data for an individual. The curve shown indicates peaks and troughs, as seen during the course of a full night's sleep whereby an individual typically has 4-5 NREM to REM sleep cycles. Thus, a time during a sleep period which correlates to one of the troughs 420, 430, and 440 within the delta power rhythm 370 may be considered preferred candidate wake times, depending upon the user's selected tolerance of sleep inertia or requirement for refreshment upon awakening. Awaking a user at a time correlating to one of the troughs 420, 430, or 440 within the delta power rhythm 370 may therefore result in greater recovery and refreshment from the sleep period compared to other portions and particularly compared to relative peak periods for deeper sleep 425 and 435, which are typically non-optimal times to awaken a user in the data shown.

Pertaining to delta power, high points in delta power curve may indicate stages of deeper sleep, while low points may indicate stages of light sleep. An individual with long wake history or high sleep debt may exhibit a delta power rhythm with more time spent in deep sleep, hence there may be increased amplitudes in delta power peaks and shallower troughs.

Figure 5:
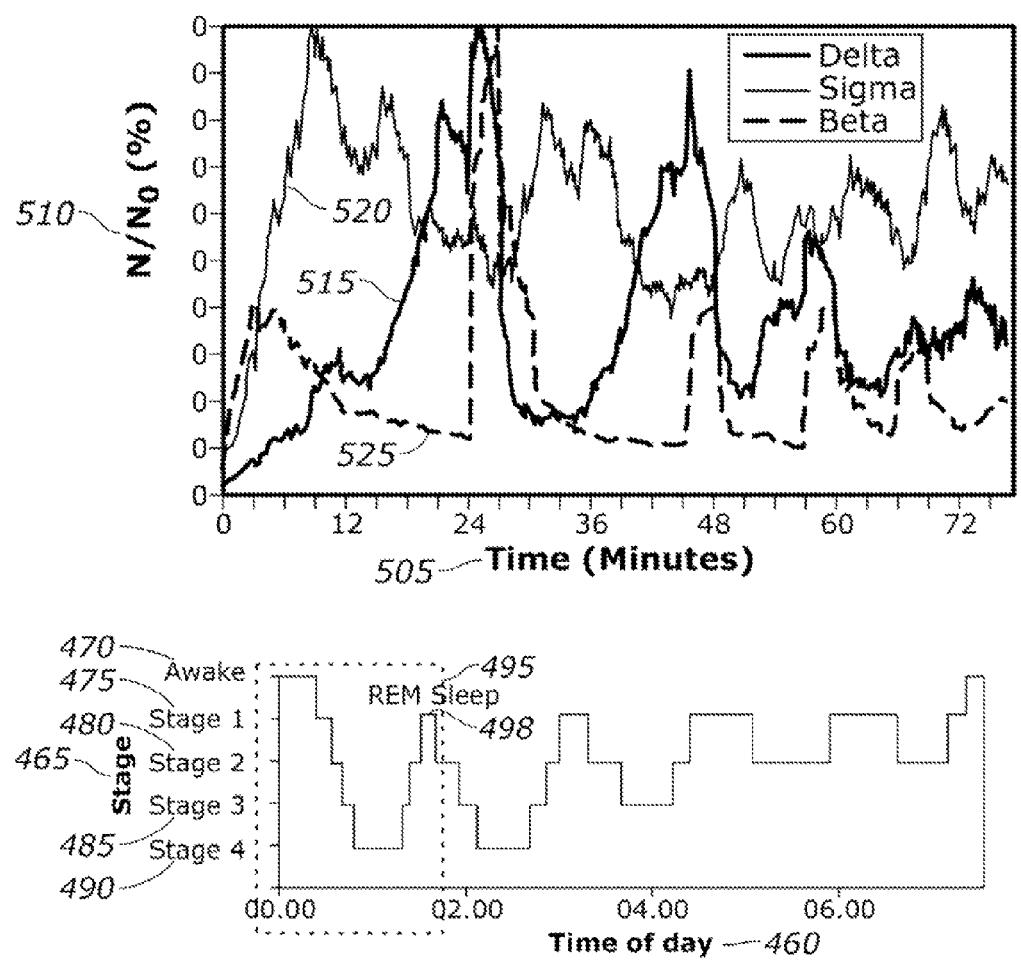
FIG. 5 provides data representing multiple frequency bands during a sleep period corresponding to sleep stages and the time of day.

Moving to FIG. 5, a schematic is provided at the bottom showing the sleep stages 465 exhibited by several subjects at particular times of day 460 over a single night time sleep cycle. The top of the figure illustrates various brain activity exhibited by several subjects or users during a sleep period corresponding to the first cycle through sleep stages 465 in the subset of the time of day 460, as indicated by the dotted boxed region 495, similar to the display format in FIG. 4. Various frequency bands such as a delta band 515, a sigma band 520, and a beta band 525 filtered and averaged from an EEG collected from several users are illustrated corresponding to various brain activity of the users. As shown, a steady increase in power, as depicted by delta power as $N/N_0$ 510, may be exhibited over time 505 as users in light stages (e.g., REM) of sleep enter deeper stages of sleep. Conversely, a steady decrease in delta power may be exhibited in the cases where users enter light stages of sleep, such as REM, from deep sleep.

Frequency bands other than the delta power band may be analyzed to determine optimal wake time. For example, a sigma band 520 (e.g., spindle or sigma oscillation mode) associated with sigma activity (12-16 Hz) may peak during stages of light sleep, suggesting optimal wake time(s). Further, the sigma band 520 may peak approximately 10-20 minutes after the onset of a sleep period.

Further, various frequency bands may be analyzed to predict dynamics of delta power rhythm. Generally, relationships between the delta and sigma bands or the delta and beta bands may be used to predict future peaks and/or troughs in delta power rhythm. Also seen in FIG. 5, the beta band 525 is associated with beta activity (12-35 Hz) which decreases as a user progresses to a deep sleep (e.g., stages 3 or 4 of NREM sleep) and reaches a portion of its initial value when a corresponding sigma band 520 reaches its peak. The beta band 525 is at a peak when the user is in a wake stage. Alternatively, the delta band 515 correlates to delta activity (1-4 Hz) which increases as a user progresses to deeper stages of sleep and decreases as sleep approaches lighter stages or during transition to REM sleep. Thus, waking an individual at or near (e.g., rising portion of the power delta power rhythm) one of the troughs as opposed to at or near (falling portion of the power delta power rhythm) one of the peaks of the delta power rhythm 370, shown in FIG. 4, will result in a quicker recover, thus enhanced performance, and greater refreshment (i.e., feeling good) after a sleep period.

Within FIG. 5, the stages of sleep exhibited by the delta power rhythm 370, such as wake stage and light sleep correlate to the awake stage 470 and stages 1-2, respectively. Thus, the sleep stages of the delta power rhythm correlate with stages 465, 470, 475, 480, 485, 490 within one NREM to REM cycle.

Figure 6:
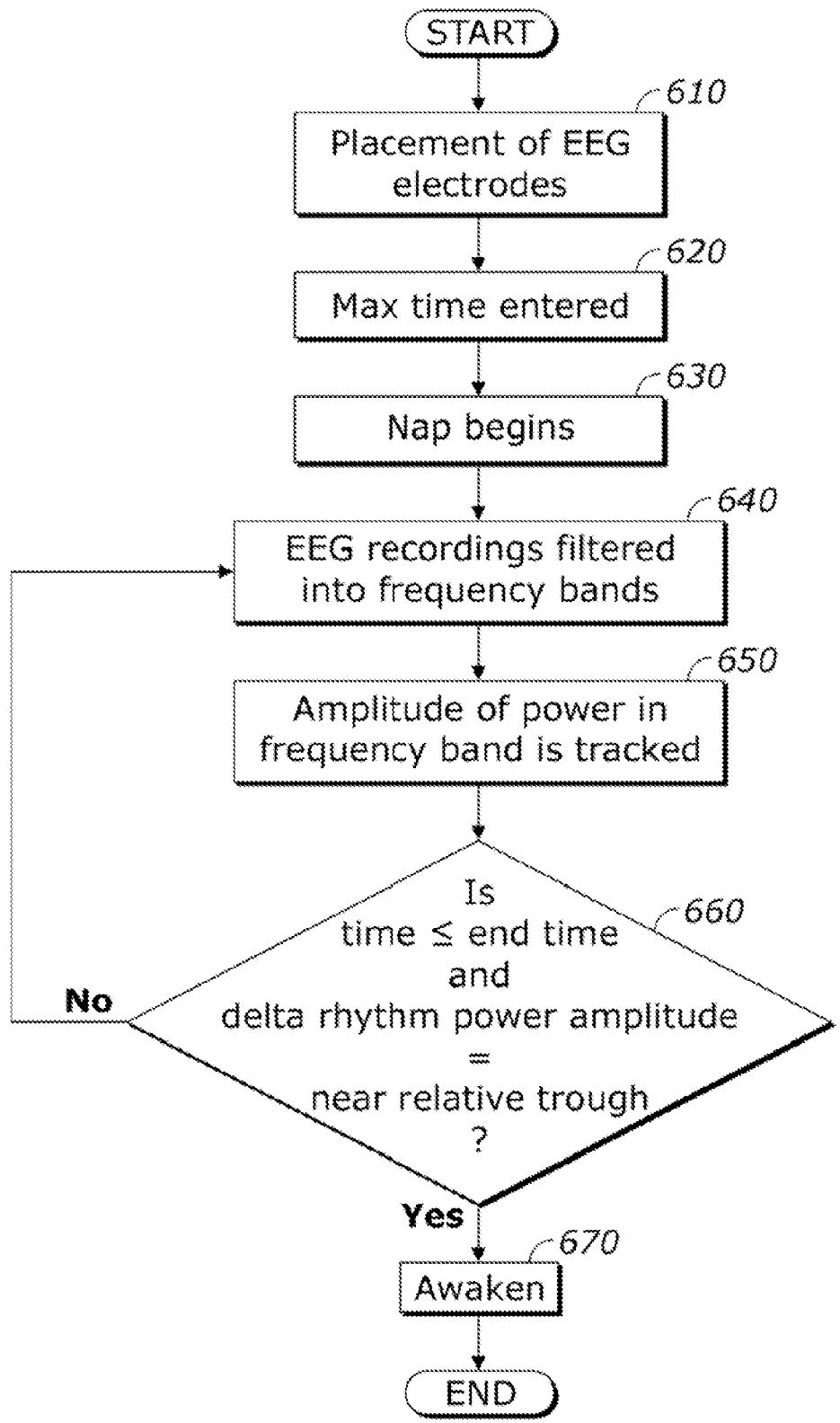
FIG. 6 provides a flow diagram of a method for monitoring physiological conditions and providing optimum wake time in accordance with one aspect of the present disclosure.

Turning now to FIG. 6, a flow diagram is shown of one implementation of a method for monitoring physiological conditions and providing optimum wake times. In step 610, EEG electrodes are placed on any suitable surface of a subject to acquire data related to brain activity. For example, EEG electrodes may be placed on a subject's skin in the head region, such as shown in FIG. 2. Prior to the onset of a sleep period, a maximum time of sleep or maximum sleep period may be inputted (e.g., manually) into the delta alarm 210 as step 620. As the sleep period begins in step 630, the EEG data received by the delta alarm are filtered into frequency bands (e.g., beta, sigma, delta bands) in step 640. The EEG filtering process performed herein follows conventional filtering processes for data related to brain activity, as known to one of skill in the art.

Continuing with FIG. 6, the amplitude of power in a frequency band, typically the delta power rhythm, is tracked in step 650 for sake of comparison with power monitored throughout the sleep period. Then, in step 660, it is determined whether the time at a particular tracking point is less than the end time of the sleep period and whether a particular delta rhythm power amplitude tracked is near a relative trough (i.e., low point) in the frequency band. If both conditions apply, the subject is awakened in step 670 by any suitable type of indicator previously described. If only one or neither of conditions in step 660 occur, the delta alarm resumes collecting and filtering EEG data into frequency bands, as outlined in step 640.

Figure 7:
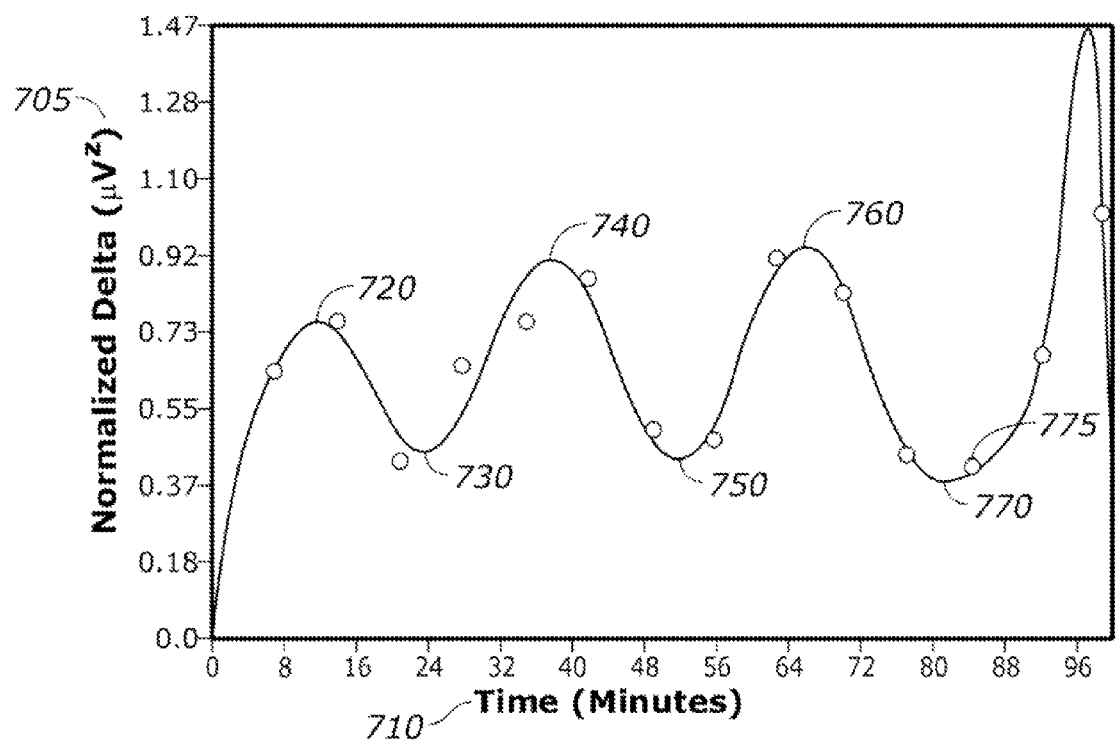
FIG. 7 provides data representing optimum wake time in accordance with one aspect of the present disclosure.

Turning now to FIG. 7, data is shown representing optimum wake time in accordance with one aspect of the present disclosure. Specifically, the delta power rhythm 370 shown depicts a curve with varying delta power 705 over time 710 in minutes. Troughs 730, 750, 770 and peaks 720, 740, 760 are shown for the delta power rhythm 370 for a sleep duration of approximately 100 minutes. Tracking point 775 is shown as merely an example to illustrate the methods shown in FIG. 6. According to step 660 of FIG. 6, the tracking point 775 will be analyzed for a first condition of whether the time is less than or equal to the end time. In the present example, the time for the tracking point 775 is approximately 85 minutes, which is less than the 100 minute duration of the sleep period. The tracking point is further analyzed for the second condition of step 660, whether the delta rhythm power amplitude is near a relative trough. As seen in FIG. 7, the tracking point 775 is near trough 770, therefore the subject is awakened at step 670.

Figure 8:
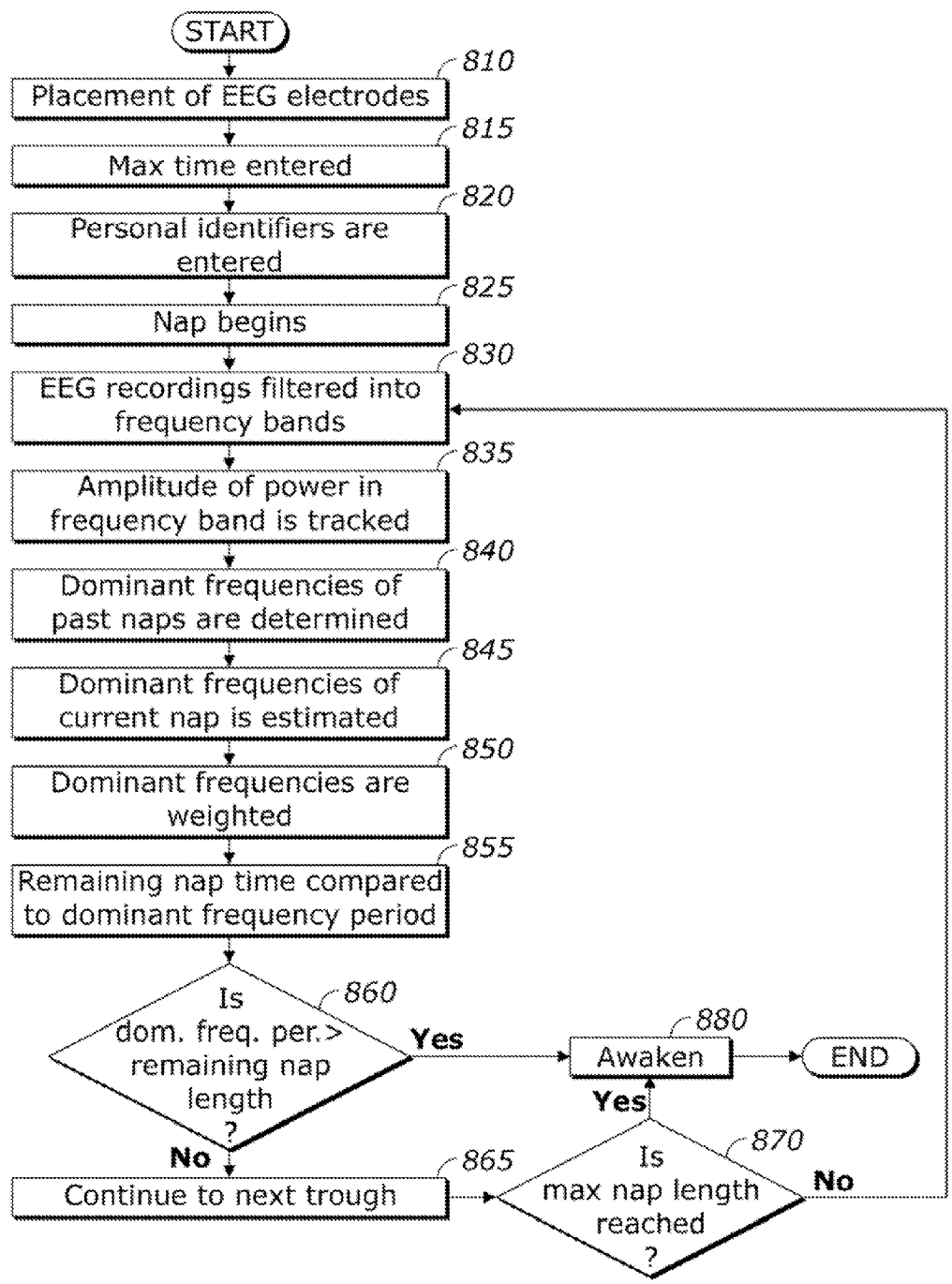
FIG. 8 provides a flow diagram of a method for monitoring physiological conditions and providing optimum wake time in accordance with another aspect of the present disclosure.

Referring now to FIG. 8, a flow diagram is shown of another implementation of a method for monitoring physiological conditions and providing optimum wake times. Similar to FIG. 6, in step 810, EEG electrodes are placed on any suitable surface of a subject to acquire data related to brain activity. For example, EEG electrodes may be placed on a subject's skin in the head region, such as shown in FIG. 2. Prior to the onset of a sleep period, a maximum time of sleep or maximum sleep duration may be inputted (e.g., manually) into the delta alarm as step 815. Personal identifiers are entered in step 820 to allow for any past records to be called for, such as from a database. As the sleep period or nap begins in step 825, the EEG data received by the delta alarm are filtered into frequency bands (e.g., beta, sigma, delta bands) in step 830. The EEG filtering process performed herein follows conventional filtering processes for data related to brain activity, as known to one of skill in the art. The amplitude of power in a frequency band, typically the delta power rhythm, is tracked in step 835 for sake of comparison with power monitored throughout the sleep period.

Continuing with FIG. 8, in step 840, dominant frequencies of past sleep periods or naps are then determined. In analyzing past sleep periods, the delta alarm 210 may determine dominant frequencies and phases of such past sleep periods. As used herein, a dominant frequency may refer to the oscillations of power in a frequency band within a given interval. In the case of a delta frequency band, power may experience slow oscillations, typically on the order of a period of seconds to minutes over a sleep interval as illustrated in FIGS. 4, 5, and 7. The dominant frequency may correspond to the peak power relative to power averaged over the course of the slow oscillations. Then in step 845, a dominant frequency of a current sleep period may be estimated. Dominant frequencies from the past and current sleep periods are then weighted in step 850 to predict troughs and peaks in the current delta power rhythm. Further, in step 855, the remaining time in the sleep duration is compared to the time period of the dominant frequency. Particularly, as troughs are detected in dominant frequencies, the delta alarm may estimate whether another trough will be encountered prior to the end of the sleep period. If it is determined that the dominant frequency period exceeds the remaining length of the sleep period in step 860, the subject may be awaken in step 880, since a maximum trough may have been reached. A maximum trough generally refers to a trough correlated with a minimum delta power within a given interval or series of troughs. Alternatively, if it is determined in step 860 that the dominant frequency period does not exceed the remaining length of the sleep period, the delta alarm may continue to the next trough of the delta power rhythm in step 865. The method is continued until the maximum length of sleep period is reach in step 870, at which time the subject is awaken in step 880. If the maximum length of the sleep period is not yet reached, the delta alarm resumes filtering EEG data into frequency bands in step 830.

Systems and methods of the present disclosure may take in consideration factors such as brain activity as reflected in EEG data, sleep debt, sleep propensity and other factors to determine optimum wake time from a sleep period. An optimum wake time may result in the greatest amount of recovery and refreshment from the sleep period and thus, enabling optimal work performance or improvement in work performance as a result. The disclosed systems and methods may include analyzing EEG filtered bands to determine low points (i.e., troughs) in delta power rhythm which correlate to an optimum time to wake a user from a sleep period, within a sleep cycle or across successive sleep cycles, to optimize the refreshment the user receives from the sleep.

Furthermore, methods of the present disclosure, detailed description and claims may be presented in terms of logic, software or software implemented aspects typically encoded on a variety of storage media or storage medium including, but not limited to, computer-readable storage medium/media, machine-readable storage medium/media, program storage medium/media or computer program product. Such storage media, having computer-executable instructions, may be handled, read, sensed and/or interpreted by a computer. Generally, computer-executable instructions, such as program modules, may include routines, programs, objects, components, data structures, and the like, which perform particular tasks, carry out particular methods or implement particular abstract data types. Those skilled in the art will appreciate that such storage media may take various forms such as cards, tapes, magnetic disks (e.g., floppy disk or hard drive) and optical disks (e.g., compact disk read only memory ("CD-ROM") or digital versatile disc ("DVD")). It should be understood that the given implementations are illustrative only and shall not limit the present disclosure.

Although the present disclosure has been described with reference to particular examples, embodiments and/or implementations, those skilled in the art will recognize that modifications and variations may be made without departing from the spirit and scope of the claimed subject matter. Such changes in form and detail, including use of equivalent functional and/or structural substitutes for elements described herein, fall within the scope of the appended claims and are intended to be covered by this disclosure.

What is claimed is:

1. A system for determining optimum wake time, the system comprising:
   a receiver for receiving and storing electroencephalogram (EEG) data and a user-specified sleep period;
   a processor configured to:
      determine a dominant oscillation of power within a frequency band based on past EEG data received;
      generate a power profile within the frequency band based on current EEG data received; and
      determine the optimum wake time using the dominant oscillation of power to predict one of a relative low point and relative high point on the power profile proximate in time to and before the end of the user-specified sleep period; and
   an alarm including an indicator configured to provide a stimulus to wake the user at the determined optimum wake time.

2. The system of claim 1, wherein the receiver includes a sensor adapted to monitor brain activity of a user.

3. The system of claim 1, wherein the frequency band is a delta band, and wherein the processor is configured to determine the optimum wake time based on the relative low point on the power profile within the delta band.

4. The system of claim 1, wherein the receiver is an input device capable of receiving and storing data associated with circadian oscillators and wherein the determination of the optimum wake time is also based on the data associated with the circadian oscillators.

5. The system of claim 1, wherein the receiver is an input device capable of receiving and storing data associated with sleep debt or sleep propensity and wherein the determination of the optimum wake time is also based on the data associated with sleep debt or sleep propensity.

6. The system of claim 1, wherein the processor is further configured to:
   send a signal to activate the indicator during the relative low point or the relative high point corresponding to the optimum wake time.

7. A system for determining optimum wake time, the system comprising:
   a receiver for receiving and storing electroencephalogram (EEG) data and a user-specified sleep period;
   a processor configured to:
      determine a dominant oscillation of power within a frequency band based on past EEG data received;
      generate a delta power rhythm associated with sleep depth based on current EEG data received; and
      determine the optimum wake time;
         wherein the optimum wake time is determined based on using the dominant oscillation of power to predict a relative low point on the curve of the delta power as plotted against sleep cycle time;
         wherein the relative low point occurs before the end of the user-specified sleep period; and
         wherein the relative low point corresponds to the optimum wake time resulting in minimal sleep inertia; and
   an alarm including an indicator configured to provide a stimulus to wake the user at the determined optimum wake time.

8. The system of claim 7, wherein the receiver includes a sensor adapted to measure brain activity of a user.

9. The system of claim 7, wherein the receiver is an input device capable of receiving and storing data associated with circadian oscillators and wherein the determination of the optimum wake time is also based on the data associated with the circadian oscillators.

10. The system of claim 7, wherein the receiver is an input device capable of receiving data and storing associated with sleep debt or sleep propensity and wherein the determination of the optimum wake time is also based on the data associated with sleep debt or sleep propensity.

11. The system of claim 7, wherein the processor is further configured to:
   send a signal to activate the indicator during the relative low point corresponding to the optimum wake time.

12. A method for determining optimum wake time, the method comprising:
   receiving and storing electroencephalogram (EEG) data via a receiver;
   determining, using a processor, a dominant oscillation of power within a frequency band based on past EEG data received;
   generating, using the processor, a power profile within the frequency band based on current EEG data received;
   determining, using the processor, the optimum wake time;
      wherein determining the optimum wake time is based on using the dominant oscillation of power to predict one of a relative low point and a relative high point on the power profile proximate in time to and before the end of a user-specified sleep period; and
      wherein one of the relative low point and the relative high point corresponds to the optimum wake time resulting in minimal sleep inertia; and
   providing, using an alarm, a stimulus to wake the user at the determined optimum wake time.

13. The method of claim 12 wherein the frequency band is a delta band, further comprising:
   filtering the delta band to generate a delta power rhythm.

14. The method of claim 12, further comprising:
   measuring, using the receiver, brain activity of a user to collect the data.

15. The method of claim 12, wherein the data further comprises data associated with circadian oscillators and wherein determining the optimum wake time is also based on the data associated with the circadian oscillators.

16. The method of claim 12, wherein the data further comprises data associated with sleep debt or sleep propensity and wherein determining the optimum wake time is also based on the data associated with sleep debt or sleep propensity.

17. The method of claim 12, wherein the frequency and phase of the dominant oscillation determines the relative low point or the relative high point on the power profile corresponding to the optimum wake time.

* * * * *

UNITED STATES PATENT AND TRADEMARK OFFICE
CERTIFICATE OF CORRECTION

PATENT NO. : 8,948,861 B2
APPLICATION NO. : 13/077557
DATED : February 3, 2015
INVENTOR(S) : Deepti Dunichand Rai et al.

It is certified that error appears in the above-identified patent and that said Letters Patent is hereby corrected as shown below:

On the Title Page
Item (75) Please delete "Mumbal" and add --Mumbai--.

In the Abstract
Item (57) in Line No. 2, please delete "comprising".

In the Drawings
In Fig. 8, Element 845, please delete "is" and insert --are--.

In the Specification
In Column 1, Line No. 21, please delete the second ",".
In Column 1, Line No. 45, please delete "1".
In Column 1, Line No. 60, please insert --a-- after "from".
In Column 6, Line No. 38, please insert --the-- before "light/dark".
In Column 6, Line No. 53, please delete "exists" and insert --exist--.
In Column 7, Line No. 30, please insert a --,-- after "Further".
In Column 7, Line No. 37, please insert --/-- after "and" and before "or".
In Column 11, Line No. 36, please insert --the-- before the second "delta".
In Column 12, Line No. 18, please delete "recover" and insert --recovery--.
In Column 13, Line No. 47, please delete "awaken" and insert --awakened--.
In Column 13, Line No. 56, please delete "awaken" and insert --awakened--.
In Column 13, Line No. 64, please delete "enabling" and insert --enable--.

Signed and Sealed this
Twenty-first Day of July, 2015

Michelle K. Lee
*Director of the United States Patent and Trademark Office*